United States Patent
Taylor

(10) Patent No.: US 11,273,247 B1
(45) Date of Patent: Mar. 15, 2022

(54) AIRWAY MANAGEMENT DEVICE

(71) Applicant: Vernon Bradley Taylor, Atoka, TN (US)

(72) Inventor: Vernon Bradley Taylor, Atoka, TN (US)

(73) Assignee: Vernon Bradley Taylor, Atoka, TN (US)

( * ) Notice: Subject to any disclaimer, the term of this patent is extended or adjusted under 35 U.S.C. 154(b) by 197 days.

(21) Appl. No.: 16/432,778

(22) Filed: Jun. 5, 2019

Related U.S. Application Data

(60) Provisional application No. 62/680,645, filed on Jun. 5, 2018.

(51) Int. Cl.
| | | |
|---|---|---|
| *A61M 1/00* | (2006.01) | |
| *A61B 17/24* | (2006.01) | |
| *A61B 17/30* | (2006.01) | |
| *A61B 17/00* | (2006.01) | |

(52) U.S. Cl.
CPC .............. *A61M 1/86* (2021.05); *A61B 17/24* (2013.01); *A61B 17/30* (2013.01); *A61B 2017/00477* (2013.01); *A61B 2017/305* (2013.01); *A61B 2217/005* (2013.01); *A61M 2210/065* (2013.01)

(58) Field of Classification Search
CPC ....... A61B 17/30; A61B 17/24; A61B 17/242; A61B 2017/00477; A61B 2217/005; A61B 2017/305; A61B 2017/306; A61M 1/0086; A61M 1/009; A61M 2210/065
See application file for complete search history.

(56) References Cited

U.S. PATENT DOCUMENTS

| | | | | |
|---|---|---|---|---|
| 5,645,075 | A * | 7/1997 | Palmer | A61B 10/0266 600/562 |
| 5,951,488 | A * | 9/1999 | Slater | A61B 10/06 600/564 |
| 6,110,127 | A * | 8/2000 | Suzuki | A61B 10/06 600/564 |
| 6,142,957 | A * | 11/2000 | Diamond | A61B 10/0266 600/567 |
| 2008/0255427 | A1 * | 10/2008 | Satake | A61B 17/083 600/204 |
| 2011/0106073 | A1 * | 5/2011 | Mueller | A61B 18/1492 606/41 |

* cited by examiner

*Primary Examiner* — Kathleen S Holwerda
*Assistant Examiner* — Uyen N Vo
(74) *Attorney, Agent, or Firm* — Haynes and Boone, LLP

(57) ABSTRACT

The present invention is directed to an improved suction catheter that increases the effectiveness of clearing the airway by way of non-limiting example, reducing the need for separate suctioning and foreign body grasping instruments. The embodiments described herein provide medical personnel the ability to use one hand and catheter to selectively grasp an anatomically lodged foreign body while reducing the likelihood of lumen blockage and interruption of suction.

7 Claims, 9 Drawing Sheets

AIRWAY MANAGEMENT DEVICE

CROSS-REFERENCE TO RELATED APPLICATIONS

This application is a nonprovisional patent application of U.S. Ser. No. 62/680,645 filed Jun. 6, 2018, under 35 U.S.C. § 111(a) (hereby specifically incorporated herein by reference).

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING, COMPACT DISC APPENDIX

None.

BACKGROUND OF THE INVENTION

The present invention is in the technical field of airway management. More particularly, in some particular implementations, this invention relates to an improved oropharyngeal device that can be used to suction viscous fluids and selectively grasp and remove foreign bodies.

It is a known practice of emergency and medical personnel to use instruments and suction catheters to clear the mouth and oropharyngeal cavity (airway) of gastric contents and body fluids (viscous fluids). The proximal and distal ends of these devices are connected by a conduit capable of transporting fluids when the proximal end is connected by a vacuum hose to a negative pressure device. It is also a known practice of emergency and medical personnel (medical personnel) to use non-suctioning, anatomically contoured instruments such as Magill forceps to grasp items that cannot be efficiently suctioned or scooped including dental fragments, large food particles, chewing gum, and coins (foreign bodies). When clearing the airway, the primary objective of Magill forceps is to precisely grasp and remove foreign bodies while suction of the oropharyngeal cavity is maintained by use of the suction catheter. Medical personnel prefer expeditious evacuation of the airway to return unobstructed breathing to the patient and prevent aspiration of viscous fluids and foreign bodies (unwanted matter). The precise use of separate suctioning and grasping catheters also restrict the use of one hand of attending medical personnel in an emergency situation. In addition, medical personnel must pay special visual attention to the anatomical structures of the airway since they limit both the size and movement of catheters used for the removal of unwanted matter. This restriction of anatomical space is further exacerbated when additional instruments such as laryngoscopes are used for visualization of anatomy and potential foreign bodies.

Known suction catheters are adapted for insertion into the oropharyngeal cavity of a patient and are inefficient at precisely grasping and removing anatomically lodged foreign bodies while maintaining suction. Often, when low viscous fluids and foreign bodies are encountered, blockage of the suctioning device frequently ensues, and removal of the catheter is necessary. When this occurs, medical personnel must momentarily take their eyes off the patient, use at least one hand to clear the obstruction or obtain a replacement device, and reintroduce a working catheter into the airway. In emergency situations, the additional time needed to restart the process of removing unwanted matter can jeopardize the health or life of the patient. To prevent this situation, larger lumen suctioning catheters have been used to help prevent blockage of the catheter but use of excessive suction to dispel debris in close proximity to delicate tissue may result in additional trauma to the fragile structures of the airway. Moreover, suction devices with spoon shaped tips do not offer sufficient rotational mobility of the catheter without spilling the unwanted matter residing within the scoop portion of the spoon.

There are currently no devices that allow medical personnel to optionally add a grasping and removal feature to existing inexpensive suction instruments or catheters. It is also desirable for suction catheters to grasp and remove unwanted matter in the presence of insufficient, intermittent, or absence of vacuum. While prior apparatuses like those disclosed in U.S. Pat. Nos. 7,938,794 and 5,665,080 provide suction and potential for debris removal, there remains a need for suction catheters to be able to provide suction in the presence of blockage of the lumen. The device described herein overcomes one or more deficiencies of the prior art.

BRIEF SUMMARY OF THE INVENTION

The inventive subject matter includes: a suction catheter of a size suitable for insertion into a body cavity made of an elongated suction tube formed of a polycarbonate, acrylic, plastic, or suitable material having a lumen running interiorly thereof, the tube having an distal suction tip with an opening for placing the lumen in communication with the interior of the body cavity and a proximal end adapted to place the lumen in communication with a source of pressure lower than that existing at the distal end of the tube, wherein the improvement includes: a slidably disposed grasping housing affixed to the outside of the catheter. More specifically, the present invention provides a suction catheter with a slidably disposed grasping housing affixed to the outside of the catheter and used by medical personnel to facilitate selective grasping and removal of unwanted matter within the airway.

In one aspect, the device is made of a substantially hollow suctioning tube coupled to an elongated grip or handle. The device is attached to a suction hose and negative pressure device well known within the art and capable of transporting unwanted matter from the distal end of the device through the proximal end of the handle. In another aspect, the distal end of elongated grip or handle may contain an integrated finger rest to increase ergonomics and provide greater operational control of the device. The proximal end of the handle comprises a vacuum attachment port with compression rings configured to receive and seal to the interior of a vacuum hose.

In yet another aspect, the distal end of the elongated suction tube includes a suction tip that has an auxiliary suction channels longitudinally extending with and in fluid communication to the interior lumen of the device to facilitate continued removal of viscous fluids in the event of blockage of the lumen. In yet a further aspect of the device, the distal end of the suctioning tube terminates into a radiused tip with radiused top and bottom portions separated by reduced radius lateral sides which allow better anatomical visualization by medical personnel. In another aspect, the lateral sides of the suction tip may contain at least one optional orifice that is in fluid communication with the lumen and allows lateral vacuuming and removal of unwanted matter.

In a one embodiment, the suction catheter assembly includes a slidably disposed grasping housing adapted to attach to the outside of catheter. The inside of the grasping housing contains at least one radius and is configured to receive the elongated suction tube and suction tip of the suction catheter. The proximal and distal ends of the grasping housing may open and close, with the left side having a male locking element and a right side having a female locking element, wherein the interface of the male and female elements lock and secure the grasping housing to the suction catheter when downward compression is applied to the interface of the locking elements. However, it will be appreciated that the proximal and distal segments of the grasping housing may be optionally or permanently attached to the suction catheter device by other means including gluing, bonding, compression fitting, or thermal securement. Moreover, the slidably disposed grasping housing may be sufficiently flexible to accommodate the existing curvatures of other suction catheters.

In one embodiment, a thumb rest is located on the top portion of the proximal end of the grasping housing. The distal end of the grasping housing contains a plurality of at least two grasping arms which are configured to curve around the perimeter of the radiused sections of the suction tip and extend to the inside radius of the lumen.

In another embodiment, the inside radius of the terminating ends of the grasping arms are configured to serve as grasping tips for the removal of foreign bodies and unwanted debris. It is appreciated that the terminating ends of the grasping tips may be blunt, sharp, serrated, or otherwise configured to grasp and retrieve a foreign body.

In yet another embodiment, opening and closing of the grasping arms and grasping tips are activated by extension and retraction displacement of the thumb rest located on the top of the proximal end of grasping housing. As the grasping housing is advanced distally away from the proximal end of the handle, movement of the suction tip within the inside taper of the diametrically opposed grasping arms forces the grasping tips to expand. The expansion of the grasping tips facilitates grasping and removal of a foreign body. Further distal advancement of the grasping housing causes the suction tip to engage a chamfer connected to a recess towards the proximal end of medial walls of the grasping arms. The recess within the medial walls of the grasping arms is configured to receive the suction tip. Entry of the suction tip into the recess allows the grasping arms and grasping tips to retract from their expanded state and engage a foreign body. Furthermore, the grasping tips may be expanded and retracted to engage a foreign body in the absence or presence of suction through the Suction device. Medical personnel may optionally retain the foreign body in the grasping tips and continue suction while the foreign body is displaced a distance away from the suction tip or continue suction and removal of unwanted matter through the lumen while the foreign body is retracted closer to the suction tip. At the discretion of the medical personnel, the grasping housing may be fully retracted for removal of the foreign body from the grasping tips.

The inventive subject matter further includes a catheter device of a size suitable for insertion into a body cavity comprising an elongated suction tube having a lumen running interiorly thereof, wherein the elongated suction tube is of a shaped to accommodate clearance of foreign bodies, the tube having an distal suction tip with an opening for placing the lumen in communication with the interior of the body cavity and a proximal end adapted to place the lumen in communication with a source of pressure lower than that existing at the distal end of the tube within a grasping housing, the distal end of the elongated suction tube made of an at least two sets of pegs; a grasping housing slidably disposed around at least a portion of the elongated suction tube and the distal suction tip, wherein the grasping housing is comprised of an at least one radius and the radius is configured to receive the elongated suction tube and distal suction tip of the suction catheter, wherein the grasping housing is made of an upper grasping arm and a lower grasping arm, wherein the at least two sets of pegs of the elongated suction tube are configured to engage with a plurality of slot ramps on the grasping arms.

The inventive subject matter further includes a method to selectively grasp and remove unwanted matter during a medical procedure on a patient involving suction, using a single instrument by providing the steps of: inserting a suction catheter into the airway or cavity of a patient; wherein the suction catheter is made of: an elongated suction tube having a lumen running interiorly thereof, the tube having an distal suction tip with an opening for placing the lumen in communication with the interior of the body cavity and a proximal end adapted to place the lumen in communication with a source of pressure lower than that existing at the distal end of the tube within a housing, a grasping housing slidably disposed around at least a portion of the elongated suction tube and the distal suction tip, wherein the grasping housing is made of at least one radius and the radius is configured to receive the elongated suction tube and distal suction tip of the suction catheter, wherein the distal end of the grasping housing is comprised of a plurality of at least two grasping arms which are configured to curve around the suction tip and mate to the outside radius of the lumen and wherein each of the at least two grasping arms terminated in a grasping tip;
moving the grasping housing distally along an elongated suction tube whereby the two grasping arm sections grasp the unwanted matter
and retracting the grasping housing to remove the object, while providing suction through the elongated suction tube.

These and other aspects, embodiments, features, and advantages of the invention shall become fully apparent from the following detailed descriptions and accompanying drawings.

DETAILED DESCRIPTION OF THE INVENTION

Figure 1:
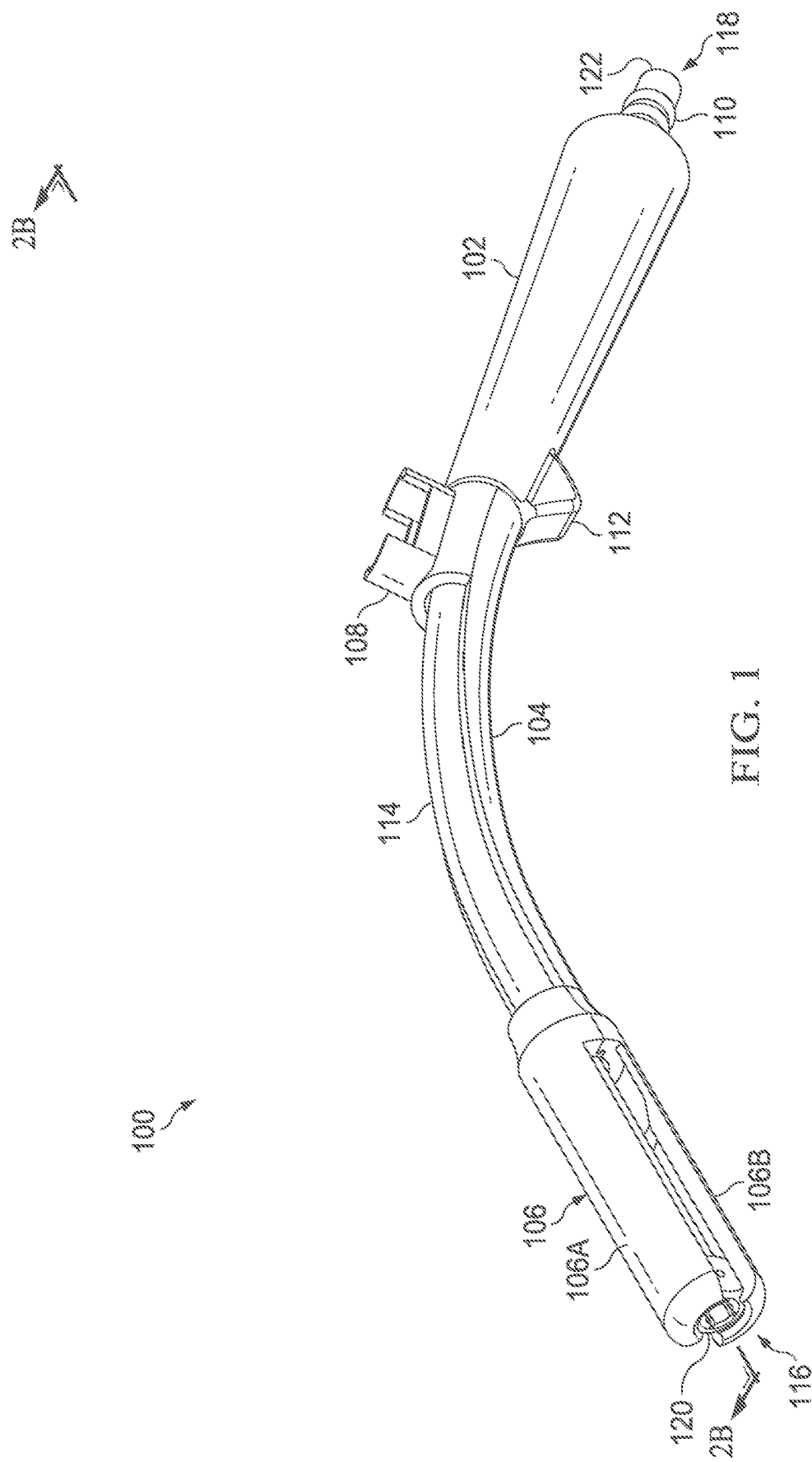
FIG. 1 illustrates a left front perspective view of the device of the present invention.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details.

Any alterations and further modifications to the described devices, and any further application of the principles of the present invention are fully contemplated as would normally occur to one skilled in the art to which the disclosure relates. In particular, it is fully contemplated that the features and components described with respect to one embodiment may be combined with the features and components described with respect to other embodiments of the present invention. In addition, dimensions provided herein are for specific examples and it is contemplated that different sizes, dimensions, and/or ratios may be utilized to implement the concepts of the present invention. To avoid needless descriptive repetition, one or more components or actions described in accordance with one illustrative embodiment can be used or omitted as applicable from other illustrative embodiments.

For the purpose of clarification and described herein, suction instrument and suction catheter may be used interchangeably and are defined as oral or other cavity suctioning catheters designed to be used by medical personnel in the oropharyngeal cavity. Moreover, mouth, airway, and oropharyngeal cavity may be used interchangeably and are defined as anatomical cavities and structures between the inferior aspect of the soft and hard palates and extending to the superior aspect of the vocal cords.

The present invention is directed to an oropharyngeal device for improved airway management by adding a slidably disposed grasping housing to the outside of a suction catheter. The improved suction catheter increases the effectiveness of clearing the airway by way of non-limiting example, reducing the need for separate suctioning and foreign body grasping instruments. For example, grasping a foreign body beyond contact with the suction tip reduces the chance of blockage of the lumen and interruption of suction. Moreover, auxiliary suction channels may help evacuate viscous fluids in the event of interruption of suction. In some instances, grasping foreign bodies beyond the tip of the suction device diminishes the likelihood of causing additional airway trauma by the suction tip. The embodiments described herein provide medical personnel the ability to use one hand and catheter to selectively grasp an anatomically lodged foreign body while reducing the likelihood of lumen blockage and interruption of suction.

In addition, some embodiments may add the ability to grasp and remove foreign bodies to existing suction catheter or instruments, thereby reducing the limitations of these inexpensive devices. In some instances, using one hand to grasp foreign bodies and evacuate the airway reduces procedure time and permits medical personnel use of their free hand to maintain control of laryngoscopes or other catheteration. The airway management device disclosed herein can optionally, cost-effectively, efficiently, and safely grasp and remove a foreign body while reducing the occurrence of interruption of suction.

Turning now to FIG. 1, the preferred embodiment of the present invention, there is shown a suction catheter device 100 constructed in accordance with the principles of the present invention. As is illustrated in the front perspective view of FIG. 1, the catheter device 100 has a proximal end 118 and a distal end 116. A handle section 102 has an elongated handle with a hollow suction port 122 at its distal end. The exterior of the suction port 122 has a set of compression fitting rings 110 configured to attach to a vacuum hose and negative pressure source. A finger rest 112 is integrated posteriorly into the distal end of the handle 102. A hollow elongated suction tube 114 extends from the distal end of the handle 102 and terminates into a suction tip 120.

The catheter device 100 includes a movably connected grasping housing 104. The grasping housing 104 can for integrally formed with the catheter device 100 or be a separate attachable unit that can be removably attached. The grasping housing 104 extends proximally to the distal end of the handle and distally to the outside of the suction tip 120. The grasping housing 104 is configured to receive both the elongated suction tube 114 and suction tip 120 and is proximally attached to the elongated suction tube 114 by a thumb rest collar 108. The thumb rest collar 108 has opposing lateral sides, approximately the width of the suction tube 114, with raised proximal and distal ends configured to receive the thumb of medical personnel. The grasping housing 104 is attached distally to the elongated suction tube 114 by a grasping arm collar 106. The grasping arm collar 106 is composed of an upper grasping arm 106A and a lower grasping arm 106B.

Figure 2A:
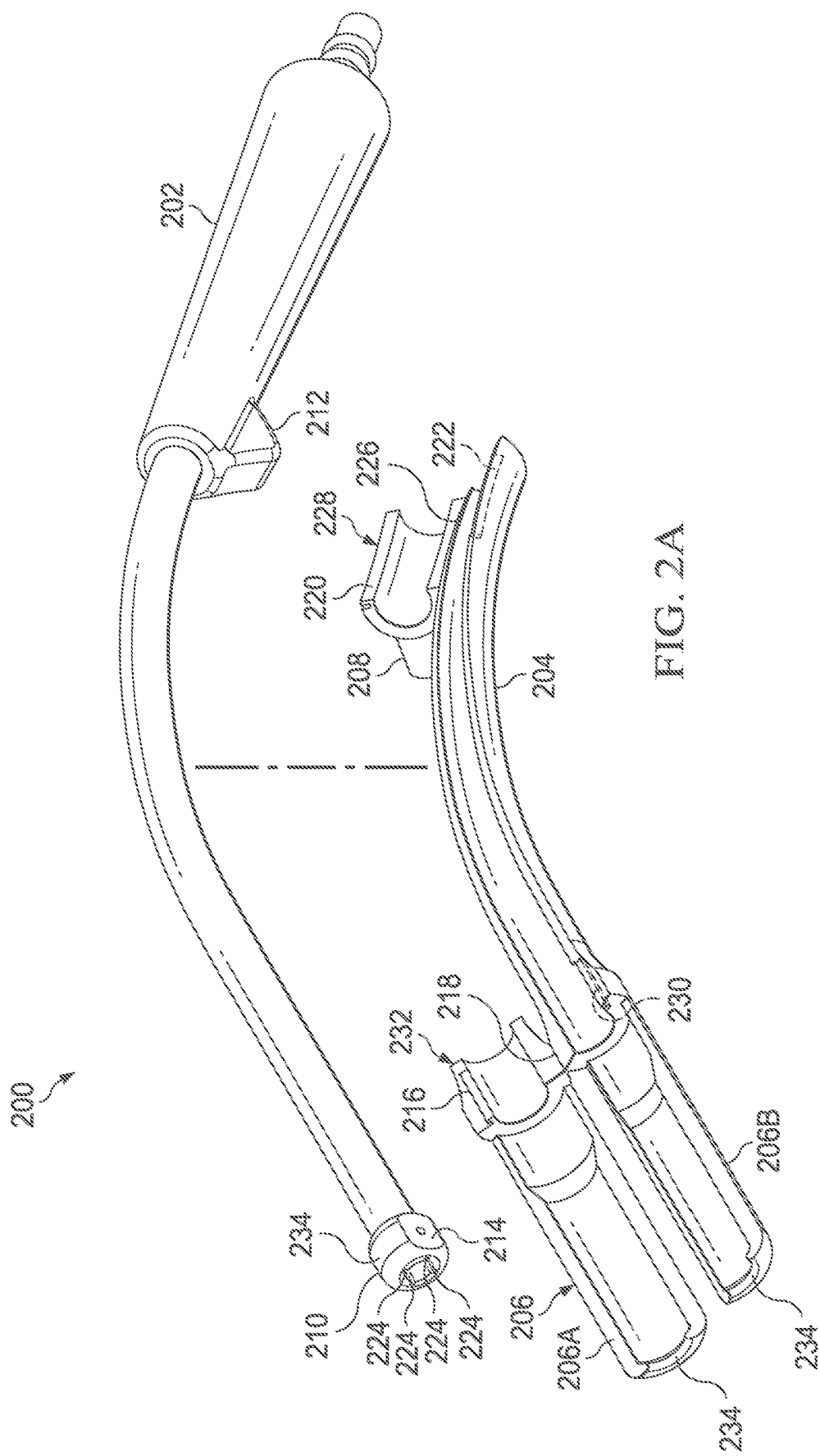
FIG. 2A illustrates a front perspective exploded view of the device of FIG. 1.
Figure 2B:
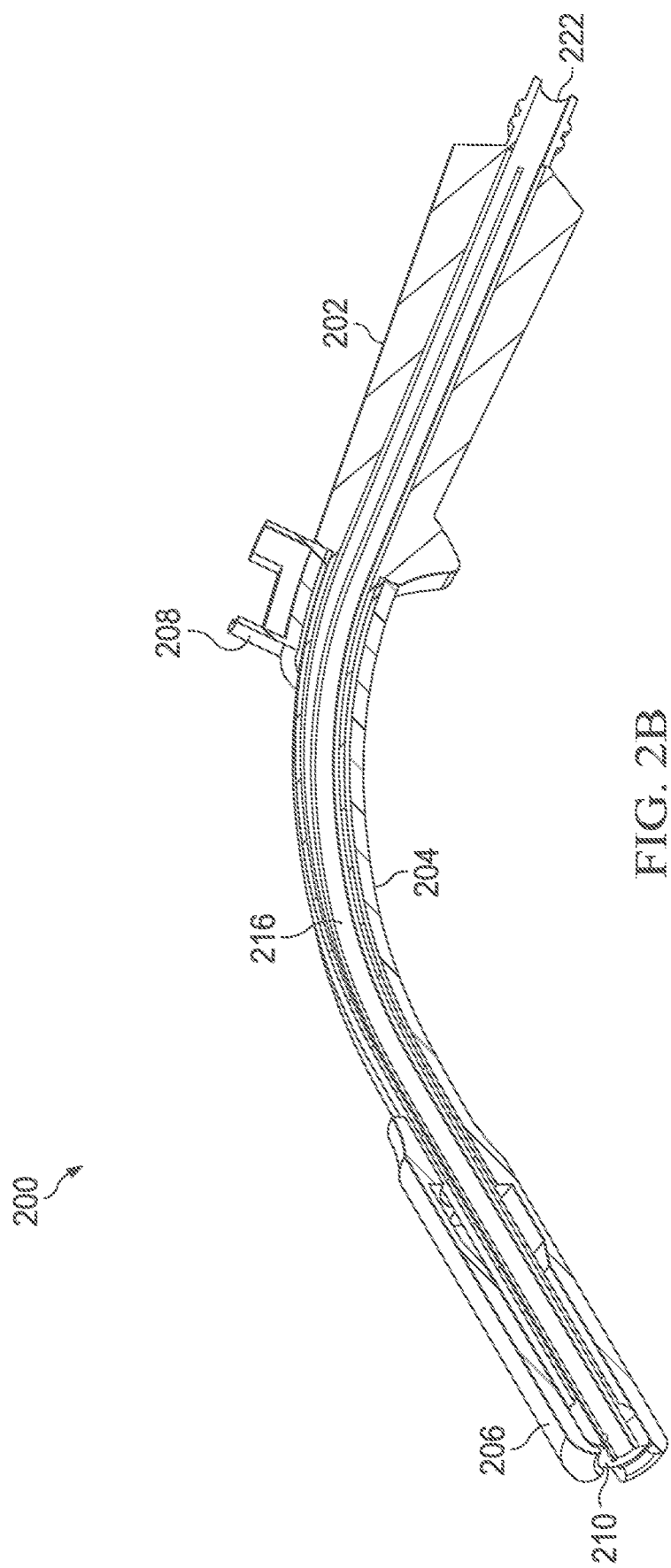
FIG. 2B illustrates a sectional view taken about lines 2B-2B of FIG. 1.

As is more clearly illustrated in FIGS. 2A-2B, the front perspective exploded view best illustrates a suction tip 210 and the attachment of a grasping housing 204 to a catheter device 200. A thumb rest collar 228 is flexibly attached to the proximal end of a grasping housing 204 by an integrated hinge 226. Moreover, the thumb rest collar 228 contains a concave anterior wall with a radius configured to receive the catheter device 200. The terminating side of the thumb rest housing 220 has a male locking element that locks into a female locking element 222 of the grasping housing 204 when the thumb rest housing 220 is rotated and closed by compression. The slidable grasping housing 204, which further includes thumb rest collar 208 and grasping arms 206, is moved back and forth along hollow elongated suction tube 214 by means of the thumb rest collar 208

Located distally of the grasping housing 204 is a grasping arm collar 232 flexibly attached by an integrated hinge 218 to the grasping housing 204. The grasping arm collar 232 contains a concave anterior wall with a radius configured to receive the device 200. A terminating side of the grasping arm collar 216 has a male locking element that locks into a female locking element 230 of t grasping housing 204 when the grasping arm collar 232 is rotated and closed by compression.

Referring still to FIG. 2A, in one embodiment and extending distally from the grasping arm collar 232 are a pair of grasping arms 206 made of an anterior grasping arm 206A and a posterior grasping arm 206B. The grasping arms 206A and 206B extend distally around the anterior and posterior segment of a suction tip 210, medially to the lumen radius of the suction tip 210 and terminate into a pair of grasping tips 234.

The suction tip 210 is integrated and attached to the distal end of the device 200 and contains a top and bottom segment that is radiused. At least one lateral side 214 is positioned between the top and bottom segment of the suction tip 210. The lateral side 214 is flat while the top and bottom portions are radiused. For large objects the grasping arms 206 need to be open a large amount, therefore most of the expansion was packaged in the first portion of sliding to minimize "pushing away" of large objects. The range of the opening distance between grasping arms 206 can be from 0.01 mm to 35 mm.

FIG. 2B illustrates a sectional view of another embodiment of the present invention. An auxiliary suction channel 210 is depicted fluidly communicating with a lumen 216 and longitudinally running from the distal end of a device 200 and terminating at the proximal end of a handle 202. The lumen 216 is shown running from the distal end of the device 200 through the proximal end of a suction port 222. The inside lumen of the suction tip 210 has a range in width of 0.1 to 20 millimeters. A plurality of auxiliary suction channels 224 fluidly connect to the lumen of the catheter device 200 and extend longitudinally from the terminating end of the suction tip 210 to the posterior end of the handle 202. Each side of the auxiliary suction channels 224 is approximately 0.5 to 1.5 mm in width. Alternatively, the auxiliary suction channels 224 are approximately one $mm^2$ each.

Figure 3A:
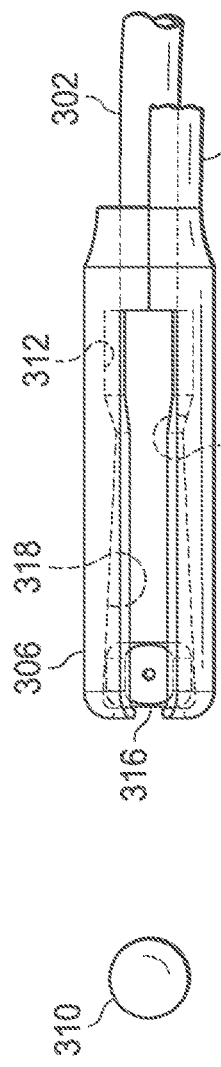
FIGS. 3(A)-3(C) illustrate three partial side views of the distal end of the device of FIG. 1.
Figure 3B:
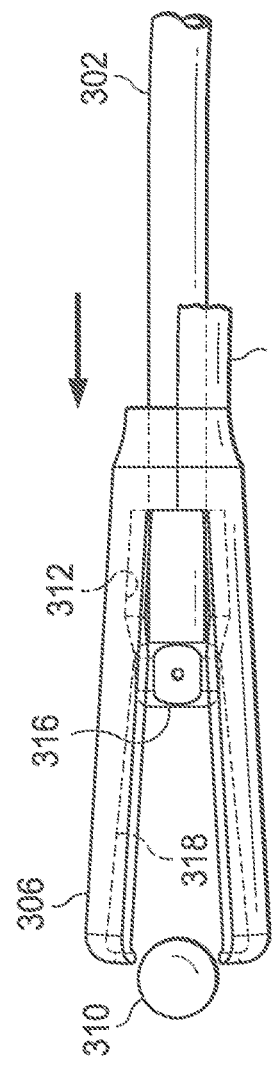
Figure 3C:
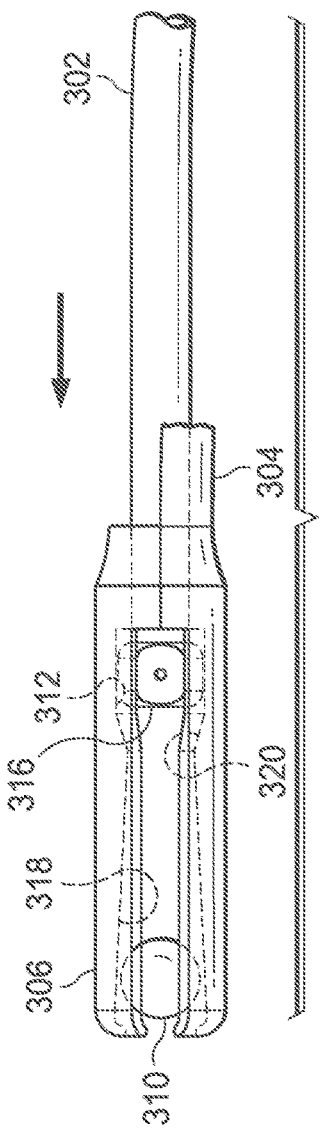

FIGS. 3A, 3B and 3C are partial side views of the present invention that illustrate the movement, position and operation of the grasping arms 306 in relation to a suction tip 316 and an elongated suction tube 302. The suction tip 316 is integrally connected to the distal end of an elongated suction tube 302. The anterior and posterior segments of the suction tip 316 are in contact with the medial sides of a pair of grasping arms 306. Commencing on the posterior side of the grasping tips, each grasping arm 306 has on its medial side a decreasing taper 318 which is distally connected to a chamfer 320. The proximal side of the chamfer 320 is attached to a recess 312 configured to receive the suction tip 316. Collectively, the lengths of the decreasing radius 318, chamfer 320, and recess 312 run approximately the length of the medial sides of the grasping arms 306.

Referring to FIG. 3A, with the grasping arms 306 in a closed (retracted position), the distal end of suction tip 316 contacts the distal end of the grasping arms. Referring now to FIG. 3B, as the grasping housing 304 is extended distally towards a foreign body 310, contact of the anterior and posterior segments of suction tip 316 along the decreasing taper 318 force the grasping arms 306 and grasping tips 322 to expand. Referring now to FIG. 3C, as expanded (opened) grasping arms 306 are positioned to grasp the foreign body 310 and the grasping housing 304 is pushed farther distally, the suction tip 310 enters the chamfer and the grasping arms 306 begin to retract. Upon entry of the suction tip 310 into the recess 312, the grasping arms 306 and grasping tips 322 are fully retracted.

In summary referring to FIGS. 1, 2A, 2B, 3A, 3B and 3C, the suction catheter can be equipped with a slidable grasping housing 204. The slidable grasping housing 204, which further includes thumb rest collar 108 and grasping arms 206, is moved back and forth along hollow elongated suction tube 114 by means of the thumb rest collar 208. The grasping housing 204 along with other elements mentioned in previous paragraph is molded or made in one piece, with both ends in a split half configuration with female locking elements 222 and 230 so that the device can be applied to hollow elongated suction tube 114 by placing it under the hollow elongated suction tube 114, folding the two halves of each end over against each other, and snapping them together with female locking elements 222 and 230.

The grasping housing 204 distal end, when assembled as described above, contains the radiused end of the suction tip 210 within it. When fully snapped together, the gripping device can be moved back and forth along the hollow elongated suction tube 114 which causes the two grasping arm sections 206A and 206B (could be more than two sections) to open or close as the decreasing radius 318, chamfer 320, and recess 312 are forced back and forth over the radiused end of the suction tip 210 by means of the thumb rest collar 208. A finger rest 212 is integrated posteriorly into the distal end of the handle 202.

Figure 4:
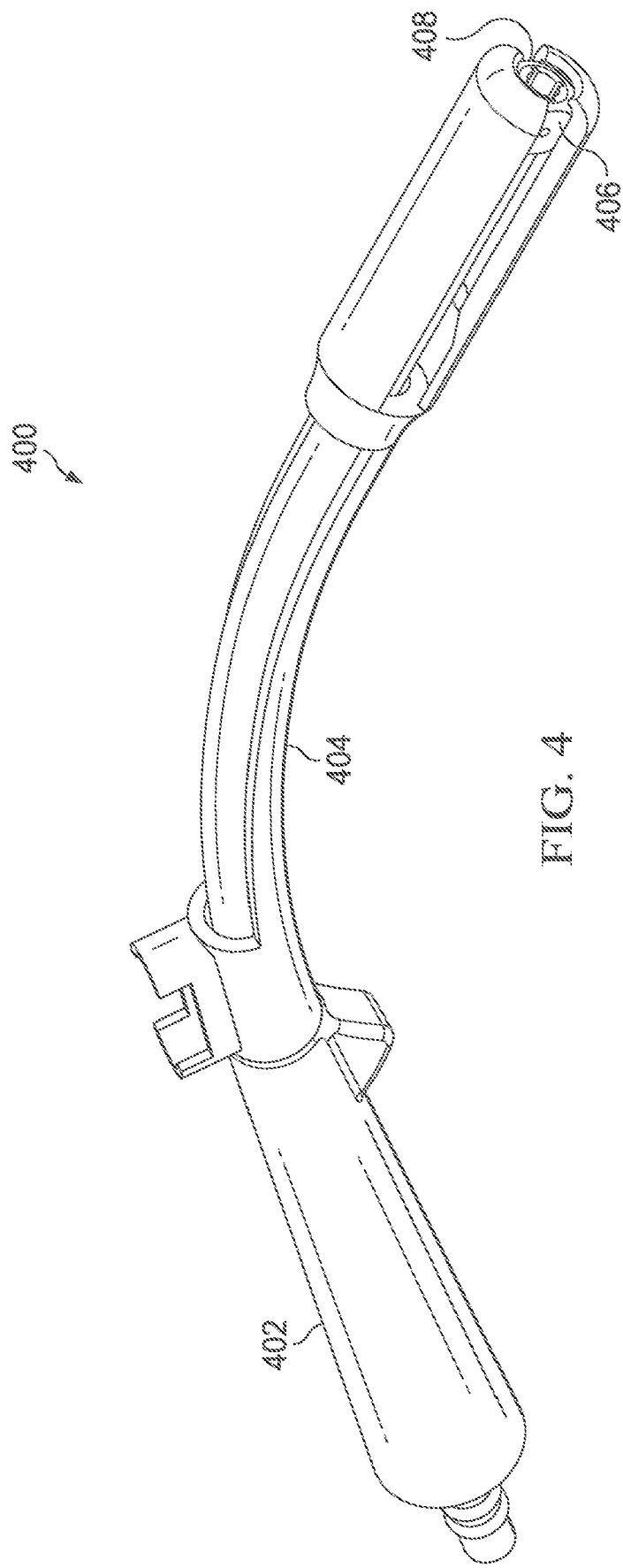
FIG. 4 illustrates a right front perspective view of the device of FIG. 1.

FIG. 4. is another embodiment illustrating a right front perspective of a device 400. The left lateral side of the suction tip 408 is depicted in this illustration. The grasping housing 404 has a grasping arm collar 406. The device 400 further includes an elongated handle 402.

The preferred dimensions of the suction devices are 20 to 26 cm. in length and the preferably internal diameter of the lumen is two to nine millimeters. Ideally, the inside diameter at the suction tip is smaller than the inside diameter at the proximal end of the handle. Optionally, the inside diameter of the lumen can remain constant. However, the preferences of medical personnel, patient size and circumstance ultimately determine the preferred dimensions of the device.

Figure 5:
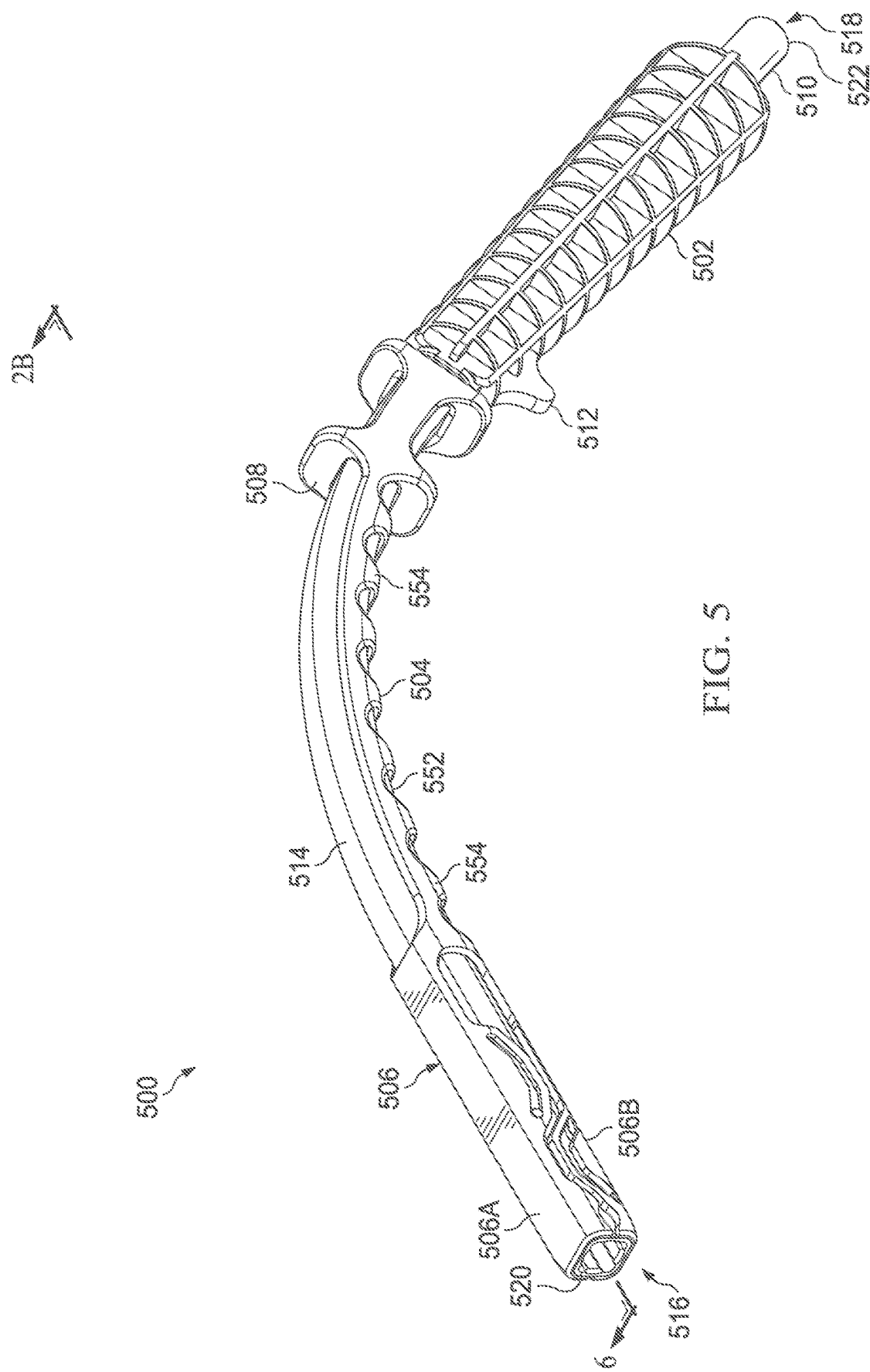
FIG. 5 illustrates a left front perspective view of the device of the present invention.
Figure 6:
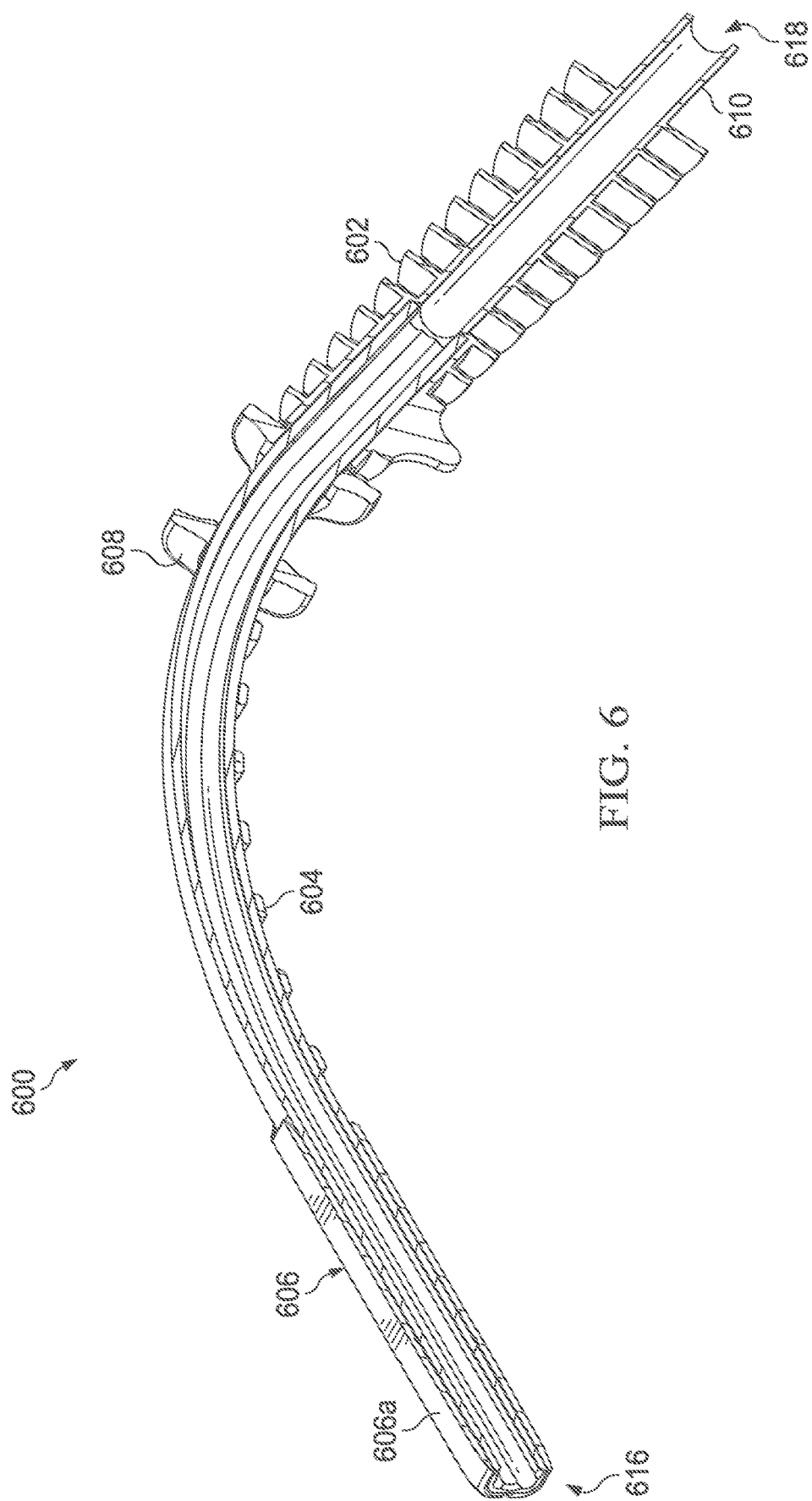
FIG. 6 illustrates a left front perspective view of the device of the present invention

Now referring to FIGS. 5-6, a catheter device 500, 600 is shown in accordance with the principles of the present invention. The catheter device 500, 600 has a proximal end 518, 618 and a distal end 516, 616. A handle section 502, 602 has an elongated handle with a hollow suction port 522 at its distal end. The exterior of the suction port 522 has a set of compression fitting rings 510, 610 configured to attach to a vacuum hose and negative pressure source. A finger rest 512 is integrated posteriorly into the distal end of the handle 502. A hollow elongated suction tube 514 extends from the distal end of the handle 502 and terminates into a suction tip 520. In an exemplary embodiment, the hollow elongated suction tube 514 is squarely shaped.

Attached to the outside of the device 500, 600 is a movably connected grasping housing 504, 604. The grasping housing 504 extends proximally to the distal end of the handle and distally to the outside of the suction tip 520. The grasping housing 504 is configured to receive both the elongated suction tube 514 and suction tip 520 and is proximally attached to the elongated suction tube 514 by a thumb rest collar 508, 608. The elongated suction tube 514 is made of a curved suction tube of adequate radius to achieve smooth accuation of the grasping arms 506, 606. Additionally, the elongated suction tube 514 is of a shape to accommodate clearance of foreign bodies.

In this embodiment, the grasping housing 504 is configured to receive both the suction tube 514 and suction tip 520 are generally square shaped in an exemplary embodiment. The thumb rest collar 508 has opposing lateral sides, approximately the width of the elongated suction tube 514, with raised proximal and distal ends configured to receive the thumb of medical personnel. The grasping housing 504 is attached distally to the elongated suction tube 514 by a grasping arm collar 506. The grasping arm collar 506 is composed of an upper grasping arm 506A and a lower grasping arm 506B, (upper grasping arm 606a shown in FIG. 6). The grasping housing 504 has an underside 552 with a series of convex rounded projections 554 There projections assist in with the actuation of the grasping housing 504 over the elongated suction tube 514.

Now referring to FIGS. 5 and 7A-7D partial side views of the present invention illustrate the movement, position and operation of the grasping arms 706 in relation to a suction tip 716 and an elongated suction tube 714. The suction tip 716 is integrally connected to the distal end of an elongated suction tube 714. The anterior and posterior segments of the suction tip 716 are in contact with the medial sides of a pair of grasping arms 706. The elongated suction tube 714 has two sets of pegs 770 for engaging with a plurality of slots ramps 780, 781 on the grasping arms 706. More specifically, the top grasping arm 706A has a pair of back slots ramps 780. The bottom grasping arm 706B has a pair of back slots ramps 781. The shape of the ramp portion of the slots dictates the force required to open/close the grasping arms 706 as well as the expansion amount, and can be contoured accordingly to give the motion/force-per-sliding-amount desired.

The grasping housing 704 is retained to the elongated suction tube 714 because the at least two sets of pegs 770 are within closed slots ramps 780, 781. The suction catheter device 500 is assembled by elastically deforming grasping housing 704 slots ramps 780, 781 wider than the at least two sets of pegs 770, then releasing once the pegs 770 are in the slot ramp 780, 781, capturing the pegs 770 grasping housing 704 to the elongated suction tube 714.

Figure 7A:
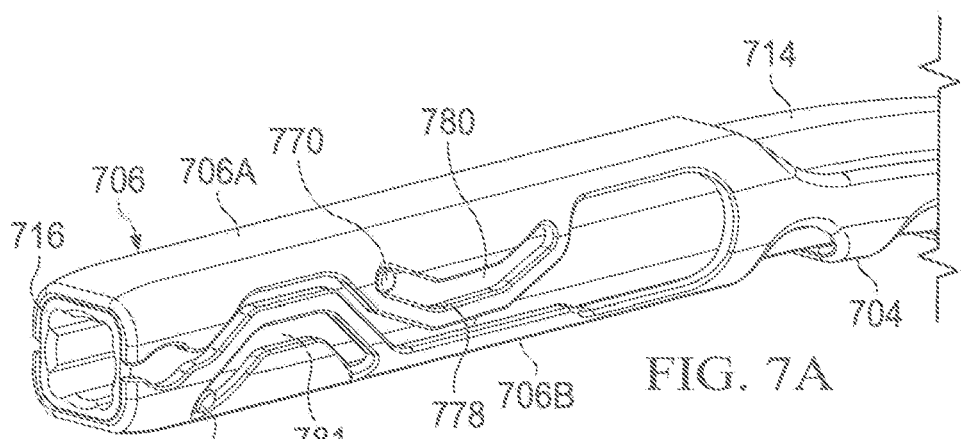
FIGS. 7(A)-7(D) illustrate three partial side views of the distal end of the device of FIG. 5.
Figure 7B:
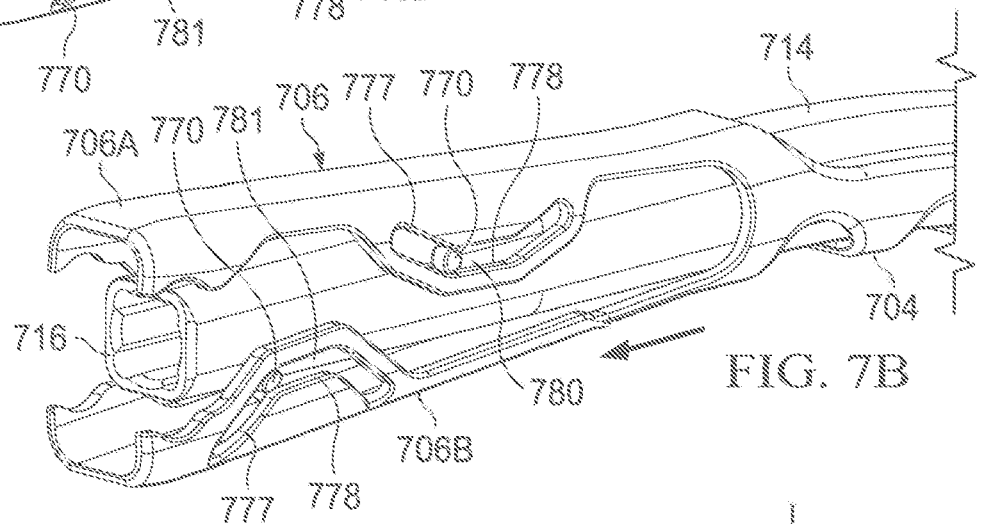

Now referring to FIG. 7B the grasping housing 704 is advanced forward and the grasping arms 706 open. As shown the grasping arms 706 are opened approximately eighty percent when the at least two sets pegs 770 are in the first semi vertical portion 777 of the slot ramps 780, 781

Figure 7C:
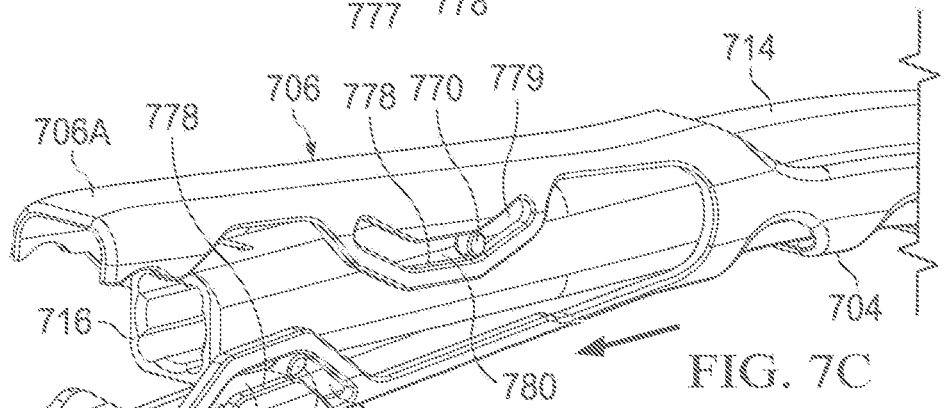

Now referring to FIG. 7C the grasping arms 706 of the grasping housing 704 is advanced forward and the grasping arms 706 open wider. The grasping arms 706 are opened the remaining twenty percent during this portion of the motion, wherein the at least two sets of pegs 770 are in the horizontal portion 778 of the slot ramps 780, 781. Specifically, the full amount of opening could be captured in the first part of the motion if desired. Generally, any XX amount of opening per YY sliding motion could be captured with the ramp/slot shape. In one exemplary embodiment, the width of the gap between grasping arms 706A and grasping arms 706B is 12.5 mm.

Figure 7D:
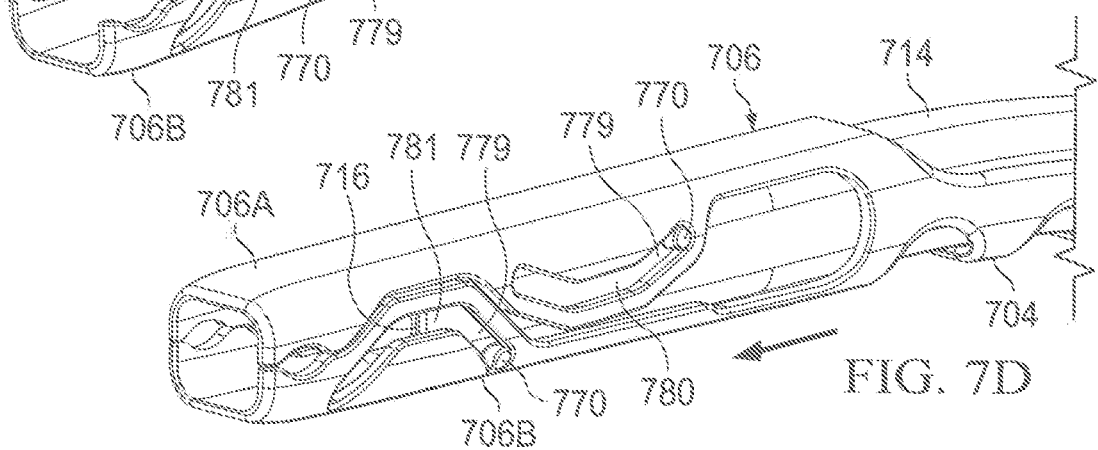

Now referring to FIG. 7D the grasping arms 706 of the grasping housing 704 is advanced forward. The grasping arms 706 are closed when the at least two sets pegs 770 are in the second semi vertical portion 779 of the slot ramps 780, 781.

Figure 8:
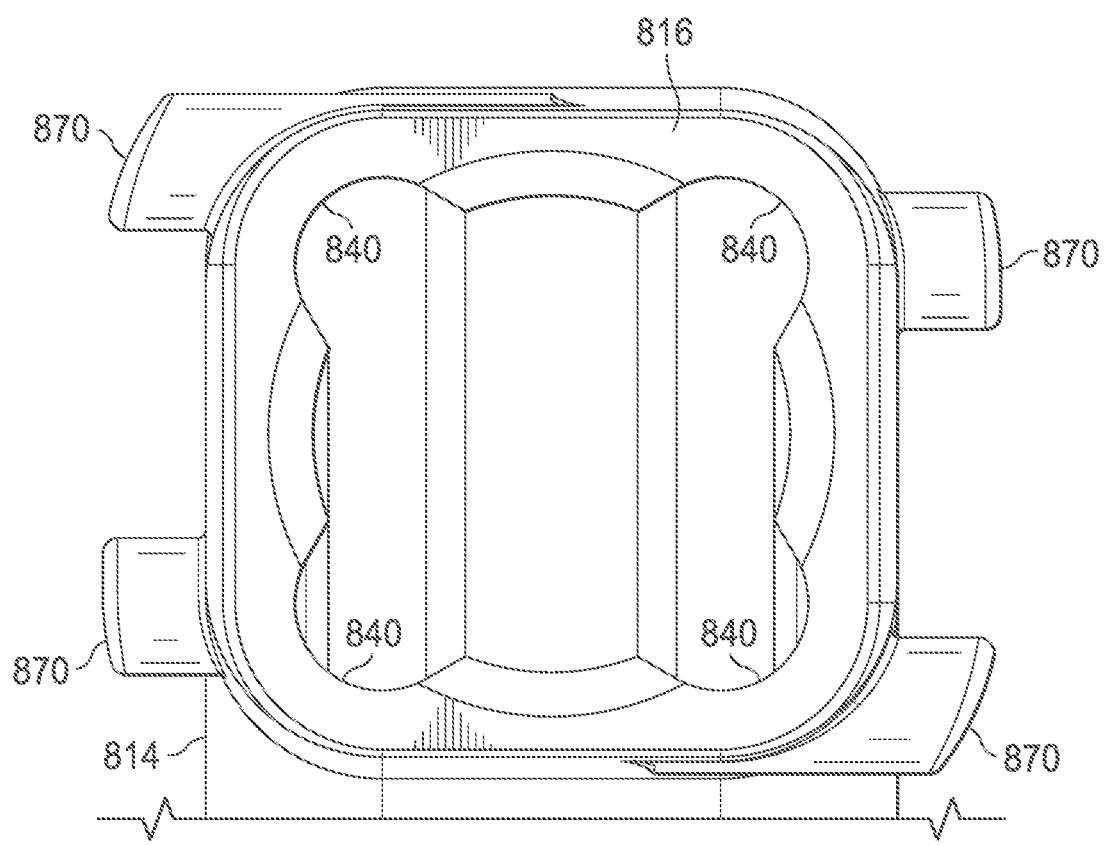
FIG. 8 illustrates a sectional view of the device of FIG. 5.

Now referring to FIG. 8, a cross-sectional view of a catheter device is shown. A main central bore 816 with four lobes 840 at the corners is provided. The two sets of pegs 870 are also shown at the corners and are off set from each other to increase structural strength of the elongated suction tube 814. The four lobes 840 allow transportation of liquid, even if the main bore is blocked with a chunk.

Benefit of this subject matter include: 1) Can force the grasping arms 706 closed in the fully retracted position providing a tight, closed profile, reducing the incidence of catching on surrounding tissue during insertion; 2) Offer prevention of the grasping arms 706 disarticulating with the inner tube during sliding if they encounter surrounding tissue, and; 3) Provide positive grasping force in the fully extended position.

This disclosure describes a novel catheter device which is specifically designed to enter the oropharyngeal cavity and has the benefits of allowing medical personnel the ability to simultaneously evacuate viscous fluids while grasping foreign bodies with a single catheter and one hand. The implementation of an extendable grasping housing fixedly or removably attached to the outside of the catheter also reduces the chance of encountering a clogged lumen and interruption of suction. Further, the device gives medical personnel the availability to grasp and remove foreign bodies in the presence or absence of suction.

Examples of suitable materials include, without limitation, metal or metal compounds, polycarbonates, acrylics, polymers, plastics, or a combination thereof. It is contemplated that the device 100 is formed by additive manufacturing, injection molding, compression molding, extrusion, casting, blow molding, machining, heat forming, joining, bonding or combinations thereof.

The invention claimed is:

1. A catheter device, comprising:
an elongated suction tube having a lumen extending from a proximal end of the elongated suction tube to a distal end of the elongated suction tube, the distal end including a suction tip comprising at least two sets of pegs; and
a grasping housing slidably disposed around at least a portion of the elongated suction tube and the suction tip, comprising an upper grasping arm, a lower grasping arm, and a grasping tip formed from an upper distal end of the upper grasping arm and a lower distal end of the lower grasping arm, the grasping housing further comprising a plurality of slot ramps on the upper and lower grasping arms configured to engage with the at least two sets of pegs of the elongated suction tube,
wherein the grasping housing is configured to extend from a first configuration to a second configuration, the first configuration comprising the grasping tip being situated in proximity to the suction tip in a closed configuration with the plurality of slot ramps engaging the at least two sets of pegs in a first slot ramp location, and the second configuration comprising the grasping tip extended a first distance distally from the suction tip in an open configuration with the plurality of slot ramps engaging the at least two sets of pegs in a second slot ramp location, and
wherein the grasping housing is further configured to extend from the second configuration to a third configuration, the third configuration comprising the grasping tip second extended a second distance distally from the suction tip in a second closed configuration with the plurality of slots ramps engaging the at least two sets of pegs in a third slot ramp location, the second distance being greater than the first distance.

2. The catheter device of claim 1, wherein:
the plurality of slot ramps in the first slot ramp location comprise a first semi vertical portion of the plurality of slot ramps, and
the plurality of slot ramps in the third slot ramp location comprise a second semi vertical portion of the plurality of slot ramps, the first and second semi vertical portions being at an angle relative to each other.

3. The catheter device of claim 1, wherein the plurality of slot ramps in the second slot ramp location comprise a horizontal portion of the plurality of slot ramps.

4. The catheter device of claim 1, wherein the grasping housing comprises a plurality of convex rounded projections formed in an underside of the grasping housing.

5. The catheter device of claim 1, wherein a range of opening distance between the upper and lower grasping arms in the open configuration ranges from 0.01 mm to 35 mm.

6. The catheter device of claim 1, wherein the at least two sets of pegs are offset from each other on lateral sides of the elongated suction tube.

7. The catheter device of claim 1, wherein the elongated suction tube further comprises a plurality of auxiliary suction channels fluidly connected to the lumen of the elongated suction tube and extending longitudinally from the suction tip to the proximal end.

* * * * *